(12) United States Patent
Wang

(10) Patent No.: US 7,651,702 B2
(45) Date of Patent: Jan. 26, 2010

(54) CROSSLINKING HYALURONAN AND CHITOSANIC POLYMERS

(75) Inventor: Wei Wang, Edinburgh (GB)

(73) Assignee: Mentor Corporation, Santa Barbara, CA (US)

(*) Notice: Subject to any disclaimer, the term of this patent is extended or adjusted under 35 U.S.C. 154(b) by 959 days.

(21) Appl. No.: 11/132,473

(22) Filed: May 19, 2005

(65) Prior Publication Data

US 2005/0271729 A1 Dec. 8, 2005

Related U.S. Application Data

(60) Provisional application No. 60/572,669, filed on May 20, 2004.

(51) Int. Cl.
*A61K 9/14* (2006.01)
(52) U.S. Cl. .................................. 424/488
(58) Field of Classification Search ................ 424/488
See application file for complete search history.

(56) References Cited

U.S. PATENT DOCUMENTS

| | | |
|---|---|---|
| 4,303,676 A | 12/1981 | Balazs |
| 4,582,865 A | 4/1986 | Balazs et al. |
| 4,957,744 A | 9/1990 | della Valle et al. |
| 4,963,666 A | 10/1990 | Malson |
| 5,162,430 A | 11/1992 | Rhee et al. |
| 5,411,874 A | 5/1995 | Ellwood et al. |
| 5,510,121 A | 4/1996 | Rhee et al. |
| 5,527,893 A | 6/1996 | Burns et al. |
| 5,550,187 A | 8/1996 | Rhee et al. |
| 5,578,661 A | 11/1996 | Fox et al. |
| 5,616,568 A | 4/1997 | Pouyani et al. |
| 5,644,049 A | 7/1997 | Giusti et al. |
| 5,677,276 A | 10/1997 | Dickerson et al. |
| 5,690,961 A | 11/1997 | Nguyen |
| 5,731,298 A * | 3/1998 | Reinmuller .................. 514/54 |
| 5,800,541 A | 9/1998 | Rhee et al. |
| 6,096,727 A | 8/2000 | Kuo et al. |
| 6,703,444 B2 | 3/2004 | Zhao et al. |
| 2002/0049281 A1 | 4/2002 | Zhao et al. |
| 2002/0091251 A1 | 7/2002 | Zhao |

FOREIGN PATENT DOCUMENTS

| | | |
|---|---|---|
| EP | 0 161 887 | 9/1991 |
| EP | 0 341 745 | 12/1994 |
| JP | 08-157378 | 6/1996 |
| WO | WO 97/04012 | 2/1997 |
| WO | WO 98/02204 | 1/1998 |
| WO | WO 99/11196 | 3/1999 |
| WO | WO 00/54762 | 9/2000 |
| WO | WO 2004/011503 | 2/2004 |
| WO | WO 2004/022603 | 3/2004 |

OTHER PUBLICATIONS

Bitter and Muir, "A Modified Uronic Acid Carbazole Reaction," *Analyt. Biochem.*, 1962, 4:330-334.
Buehler and Pearson, "Carboxylic Esters," *Survey of Organic Synthesis*, 1970, p. 802.
Bulpitt and Aeschlimann, "New strategy for chemical modification of hyaluronic acid: Preparation of functionalized derivatives and their use in the formation of novel biocompatible hydrogels," *J. Biomed. Mater. Res.*, 1999, 47:152-169.
Carraway and Koshland, Jr., "Carbodiimide Modification of Proteins," *Meth. Enzymol.*, 1972, 25:616-623.
Danishefsky and Siskovic, "Conversion of carboxyl groups of mucopolysaccharides into amides of amino acid esters," *Carbohyd. Res.*, 1971, 16:199-205.
Hardingham and Muir, "The specific interaction of hyaluronic acid with cartilage proteoglycans," *Biochim. Biophys. Acta*, 1972, 279:401-405.
Hascall and Laurent, "Hyaluronan: Structure and Physical Properties," [online]. Glycoforum/Science of Hyaluronan-1, 1997, [retrieved on Oct. 5, 2004]. Retrieved from the Internet: <URL: www.glycoforum.gr.jp/science/hyaluronan/HA01/HAO1E.html>, 10 pages.
Imoto and Yagishita, "A Simple Activity Measurement of Lysozyme," *Agr. Biol. Chem.*, 1971, 35(7):1154-1156.
Kuo et al., "Chemical Modification of Hyaluronic Acid by Carbodiimides," *Bioconjug. Chem.*, 1991, 2(4):232-241.
Kurita et al., "Preparation and biodegradability of chitin derivatives having mercapto groups," *Carbohydrate Polymers*, 1993, 20:239-245.
Kurzer and Douraghi-Zadeh, "Advances in the chemistry of carbodiimides," *Chem. Rev.*, 1967, 67(2):107-152.
Maghami and Roberts, "Evaluation of the viscometric constants for chitosan," *Makromol. Chem.*, 1988, 189:195-200.
Nakajima and Ikada, "Mechanism of Amide Formation by Carbodiimide for Bioconjugation in Aqueous Media," *Bioconjugate Chem.*, 1995, 6:123-130.
Ogamo et al., "Preparation and properties of fluorescent glycosaminoglycuronans labeled with 5-aminofluorescein," *Carbohydr. Res.*, 1982, 105:69-85.
Pouyani et al., "Solid-State NMR of N-Acylureas Derived from the Reaction of Hyaluronic Acid with Isotopically-Labeled Carbodiimides," *J. Am. Chem. Soc.*, 1992, 114:5972-5976.
Suh and Matthew, "Application of chitosan-based polysaccharide biomaterials in cartilage tissue engineering: a review" *Biomaterials*, 2000, 21(24):2589-2598.
Tomihata and Ikada, "Crosslinking of hyaluronic acid with water-soluble carbodiimide," *J. Biomed. Mater. Res.*, 1997, 37(2):243-251.
Tomihata and Ikada, "Preparation of Cross-Linked Hyaluronic Acid Films of Low Water Content," *Biomaterials*, 1997, 18(3):189-195.
Vercruysse et al., "Synthesis and in Vitro Degradation of New Polyvalent Hydrazide Cross-Linked Hydrogels of Hyaluronic acid," *Bioconjug. Chem.*, 1997, 8(5):686-694.
Zhao and Lockett, "Double Crosslinked Hyaluronan and its Medical Applications," *HA 2003 Proceedings* http://www.matrixbiologyinstitute.org/ha03/toc.htm, printed from the internet on Nov. 17, 2004, 8 pages.

* cited by examiner

*Primary Examiner*—Michael G. Hartley
*Assistant Examiner*—James W. Rogers

(57) ABSTRACT

Materials and methods related to crosslinking hyaluronan and chitosan are described herein. Also described are products of the described methods.

9 Claims, 3 Drawing Sheets

CROSSLINKING HYALURONAN AND CHITOSANIC POLYMERS

CROSS-REFERENCE TO RELATED APPLICATIONS

This application claims priority from U.S. Provisional Application Ser. No. 60/572,669, filed May 20, 2004.

TECHNICAL FIELD

This document relates to processes for crosslinking hyaluronan and chitosan, as well as to products generated using the processes described herein and uses of the products.

BACKGROUND

Hyaluronic acid is a member of a class of polymers known as glycosaminoglycans. It is a naturally occurring linear polysaccharide composed of alternating N-acetyl-D-glucosamine and D-glucuronic acid monosaccharide units linked via β-1,4-bonds, with the disaccharide units linked via β-1,3-glycoside bonds. Hyaluronic acid usually occurs as salts such as sodium and potassium hyaluronates. The sodium salt has a molecular formula of $(C_{14}H_{20}NNaO_{11})_n$ where n can vary according to the source, isolation procedure and method of determination. The molecular weight generally falls between about $6\times10^4$ and about $1.4\times10^7$. The term "hyaluronan" (HA) usually refers to both hyaluronic acid and its salts.

HA is present in the synovial fluid and the vitreous body of the eye. It also is widely distributed in the connective tissues of vertebrates, such as human umbilical cord, rooster combs and joint cartilage. HA can be isolated from all of these sources. It also can also be biosynthesized, and may be obtained using fermentation methods. For example, U.S. Pat. No. 5,411,874 describes a method for producing hyaluronic acid by continuous fermentation of *Streptococcus equi*.

HA is non-immunogenic and non-toxic. When implanted or injected into a living body, however, HA typically is degraded by oxidation and by enzymes such as hyaluronidase. Because HA is a water-soluble polymer and is degraded and eliminated rapidly in vivo, the potential applications for HA in biomedical purposes have been somewhat limited.

SUMMARY

Polyelectrolyte complexes containing, for example, HA and chitosan, typically are cloudy solids having a very limited capacity to adsorb water, and are only moderately stable in a normal pH range. This document is based in part on the discovery that by controlling pH, the formation of polyelectrolyte complexes can be avoided. For example, by adjusting the pH of solutions of hyaluronan and glycol chitosan so that the pH of the mixed solution is 7.2 or higher, formation of the complex between hyaluronan and glycol chitosan can be prevented. This can be confirmed by observation of a clear and transparent mixed solution, independent of whether the individual solutions are dilute or concentrated, and the complete dissolution of the dried cast film in distilled water.

Hyaluronan and chitosanic polymers can be covalently crosslinked in the presence of agents such as 1-ethyl-3-(3-dimethylaminopropyl) carbodiimide hydrochloride (EDC). In aqueous solution, the carboxyl groups of hyaluronan can be activated, followed by nucleophilic addition by amino groups of chitosanic polymers to form an intermolecular amide linkage. The carboxyl group of hyaluronan can be maximally activated by controlling the solution pH, while sufficient —$NH_2$ groups are unprotonated so that nucleophilic addition occurs efficiently.

In one aspect, this document features a method for covalently linking hyaluronan and chitosan. The method can include mixing a solution of hyaluronan and chitosan at a pH of at least 7.2 in the presence of a water soluble carbodiimide. The method can include the steps of: (a) providing a solution of hyaluronan with a pH of 4.0 to 4.3; (b) adding a solution of chitosan such that the resultant mixed solution has a pH of at least 7.2; and (c) adding a water soluble carbodiimide. The method can further include the step of: (d) washing the product of (c) with water or PBS. The pH of the mixed solution can be 7.2 to 7.8.

The method can further include the steps of: (d) stirring the solution formed in (c) for 3 hours at room temperature; and (e) washing the resultant hydrogel in PBS. Alternatively, the method can further include the steps of: (d) stirring the solution formed in (c) for 3 hours at room temperature; (e) washing the resultant hydrogel in PBS or water; and (f) freeze-drying the hydrogel. In another alternative, the method can further include the steps of: (d) stirring the solution formed in (c) for 30 minutes at room temperature; (e) casting the solution into a desired form and allowing it to dry; and (f) washing the resultant film with water or PBS.

The water soluble carbodiimide can be 1-ethyl-3-(3-dimethylaminopropyl) carbodiimide methiodide or 1-ethyl-3-(3-dimethylaminopropyl) carbodiimide hydrochloride (EDC), or a derivative thereof. The pH of the mixed solution can be between 7.2 and 7.5.

In another aspect, this document features a product containing hyaluronan cross linked to chitosan formed by the methods described herein. The product can be for pharmaceutical, medical, or cosmetic use, or for use in medicine or surgery. The product can be for delivery of anti-inflammatory agents, antibiotics, analgesics, anaesthetics, wound healing promoters, cytostatic agents, immunostimulants, immunosuppressants, or antivirals. For example, the product can be for the delivery of an anaesthetic such as lidocaine.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

By controlling pH, the formation of polyelectrolyte complexes can be avoided. For example, by adjusting the pH of solutions of hyaluronan and glycol chitosan so that the pH of the mixed solution is at least 7.2 (e.g., 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, or higher than 9.5), formation of a polyelectrolyte complex between hyaluronan and glycol chitosan can be prevented. Hyaluronan and chitosanic polymers can be covalently crosslinked in the presence of agents such as EDC. Thus, described herein are methods for covalently crosslinking HA to chitosan using an amidation reaction, as well as crosslinked products made by the described methods.

As used herein "hyaluronan" encompasses hyaluronic acid and its hyaluronate salts, including, but not limited to, sodium hyaluronate, potassium hyaluronate, magnesium hyaluronate and calcium hyaluronate.

"Chitosan" as used herein refers to any chitosan or chitosan derivative able to dissolve at neutral pH including, but not limited to, chitosan having a degree of deacetylation of around 50% and derived from homogeneous deacetylation of chitin, glycol chitosan, N-methyl glycol chitosan, re-N-acetylated chitosan, O-acetylated chitosan, carboxymethyl chitosan, oxidized chitosan, sulfonated chitosan and graft derivatives such as chitosan-PEG hybrid.

Water soluble carbodiimide can be, for example, 1-ethyl-3-(3-dimethylaminopropyl) carbodiimide methiodide or 1-ethyl-3-(3-dimethylaminopropyl) carbodiimide hydrochloride, or derivatives thereof.

Figure 1:
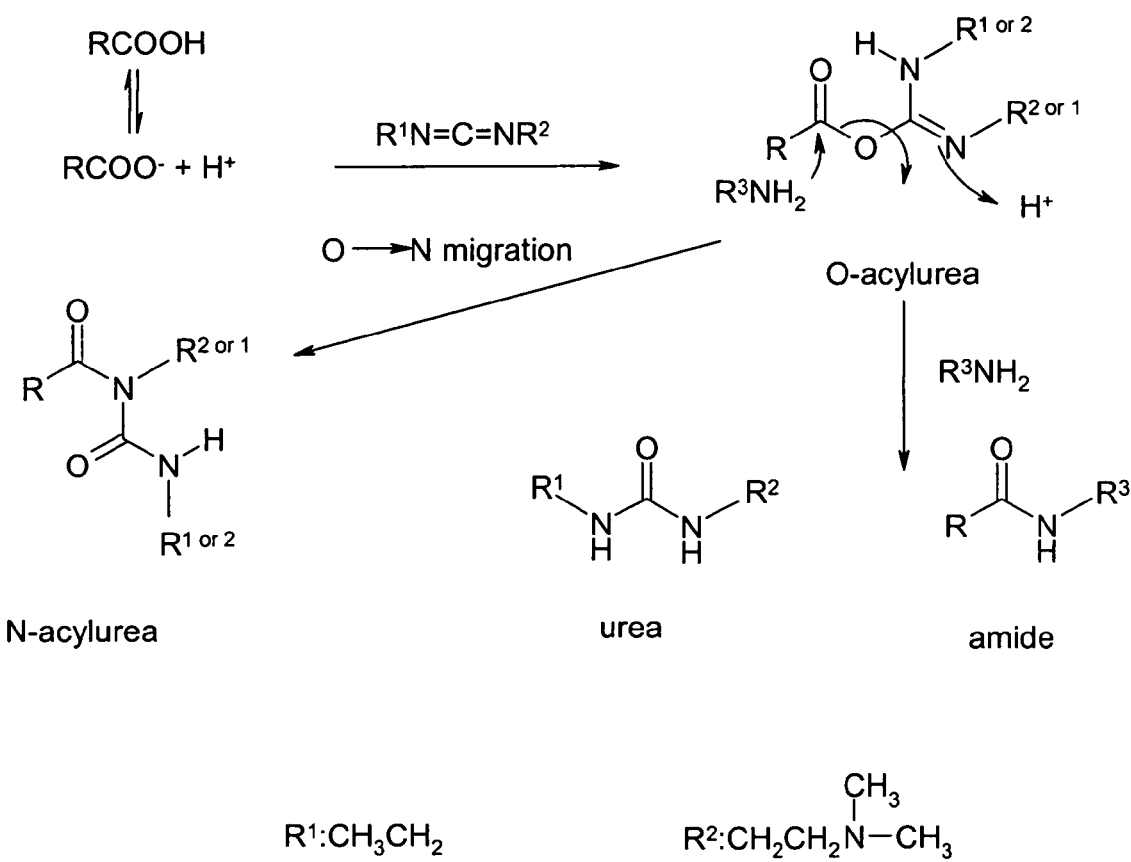
FIG. 1 shows the mechanism of the reaction between carboxylic acid and carbodiimide, with and without primary amines.

Crosslinking reactions can take place in nearly neutral pH solution in which polyelectrolyte complexes, i.e., products containing ionic bonds, cannot form. A suitable pH can be, for example, from about 7.2 to about 7.8 (e.g., 7.2, 7.3, 7.4, 7.5, 7.6, 7.7, or 7.8), or from about 7.2 to about 7.5 (e.g., 7.2, 7.3, 7.4, or 7.5). At such a pH, most carboxyl groups of hyaluronan can dissociate and most —$NH_2$ group of chitosanic polymers are unable to be protonated, so that polyelectrolyte complexes cannot form. Under such conditions, the carboxyl groups of hyaluronan can be activated by EDC, followed by nucleophilic reaction with $NH_2$ groups of chitosanic polymers in solution (see FIG. 1). During the reaction, the mixed solution can remain clear and the solution pH can increase gradually up to about 9.0. At this pH, almost all —$NH_2$ group are unprotonated, so every —$NH_2$ group has the chance to react by nucleophilic addition to form an amide bond, resulting in HA crosslinked to chitosanic polymers.

The methods provided herein can include the steps of:

(a) providing a solution of hyaluronan with a pH of 4.0 to 4.3;

(b) adding a solution of chitosan such that the resultant mixed solution has a pH of at least 7.2; and (c) adding a water soluble carbodiimide Under such mild conditions, a clear and strong hydrogel can be obtained using hyaluronan and neutral water-soluble chitosanic polymers in the presence of EDC. The strongest gel can be obtained after about 2 or 3 hours of adding EDC by controlling the weight ratio and the concentrations of the two polymers and EDC. The methods can further include (d) stirring the solution formed in (c) for 2 to 4 hours (e.g., 2 hours, 2.5 hours, 3 hours, 3.5 hours, or 4 hours) at a suitable temperature (e.g., room temperature, 15° C., 16° C., 17° C., 18° C., 19° C., 20° C., 21° C., 22° C., 23° C., 24° C., or 25° C.); and/or (e) washing the resultant product with water or PBS (e.g., PBS having pH 7.4), with or without stirring. These steps can remove side products and unreacted EDC without loss of the gel's physical properties.

A hydrogel product can be formulated into an injectable gel for various biomedical purposes. A hydrogel can be easily broken up into a microgel suitable for subcutaneous, intramuscular, or intraperitoneal injections using, for example, a Gauge 30 needle. Such gels can be used, for example, for augmentation, viscosupplementation, drug delivery, or other purposes.

Figure 2:
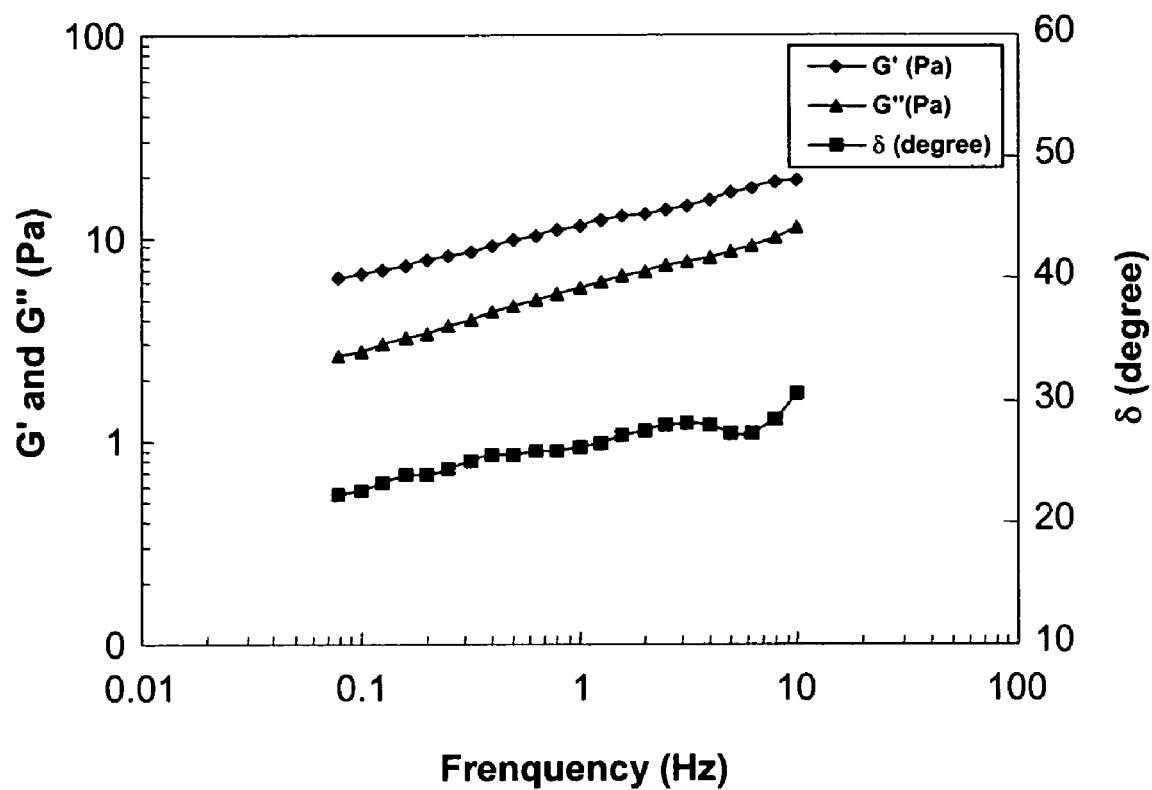
FIG. 2 shows the rheological properties of an injectable gel of crosslinked HA and glycol chitosan (T=25° C.).

The swelling ratio of the gels can be 4500-6000%. Rheological results have indicated that a gel can be soft and very elastic, and can have the typical and distinct behavior of a crosslinked network structure. The elastic modulus G' can be higher than the viscous modulus G", and they can be almost parallel to each other without an intersection of the respective curves (FIG. 2).

Crosslinking between hyaluronan and chitosanic polymers can be further confirmed by FTIR. As described herein, for example, the —$NH_2$ peak of chitosanic polymer can decrease greatly or even almost disappear, and a new peak due to the amide bond between HA and chitosan can be clearly detected.

The crosslinked HA/chitosan materials provided herein may be used in a variety of forms including, without limitation, membranes, beads, sponges, tubes, sheets, and formed implants. Thus, the methods provided herein also can be used to form water insoluble films, membranes, or sheets. Such films can be used, for example, to prevent post-operative adhesion formation on wound dressing and implants. Biomaterial films can be easily prepared by casting hyaluronan/chitosanic polymer solutions containing EDC as any desired shape, size, and thickness at an initial pH of 7.2 or higher, typically 7.2 to 7.5. For example, methods for forming a film of hyaluronan crosslinked with chitosan can include the steps of:

(a) providing a solution of hyaluronan with a pH of 4.0 to 4.3;

(b) adding a solution of chitosan such that the resultant mixed solution has a pH of 7.2 to 7.5;

(c) adding a water soluble carbodiimide;

(d) stirring the solution formed in (c) for 15 minutes to 2 hours (e.g., 15 minutes, 20 minutes, 30 minutes, 45 minutes, 1 hour, 1.5 hours, or 2 hours) at a suitable temperature (e.g., room temperature, 15° C., 16° C., 17° C., 18° C., 19° C., 20° C., 21° C., 22° C., 23° C., 24° C., or 25° C.);

(e) casting the solution into desired form, and allowing to dry; and (f) washing the film formed with excess PBS After drying, the films or membranes or sheets can be fully transparent and/or colored if needed. The films may be washed with water or PBS (e.g., PBS having pH 7.4), and can be stored either in PBS or in dried form. The films can have a good mechanical strength. In addition to their use in prevention of adhesion or accretion of body tissue during the post-operative or healing period, the films can be used for dermal wound dressing or wound healing. Further, the films can entrap drugs and then be implanted at the locus where delivery is needed or desired. The films can also be used as contact lens materials, or for cell culture and other tissue engineering purposes.

The swelling degree of films made by the methods provided herein can be between about 440% and about 1300% (e.g., 440%, 450%, 500%, 600%, 700%, 800%, 900%, 1000%, 1100%, 1200%, or 1300%). The films can be stable in 6 M HCl and 6 M NaOH aqueous solutions for at least a week. For example, some of the films made as described herein displayed no weight loss after storage for two months in PBS (e.g., PBS having pH 7.4).

Other biomaterials formed from crosslinked hyaluronan with chitosanic polymers can be prepared, such as matrices, powders, fibers and sponges. For example, biomaterial sponges can be prepared by freeze-drying the gels prepared as described herein. Powders can be formed by injecting a gel into an organic solvent such as acetone or isopropyl alcohol (IPA), or they can be prepared by cutting and crushing the crosslinked films. Fibers can be prepared by extruding the mixed solutions or by spinning a gel. A matrix can be obtained by drying a gel in air or by precipitating a gel with organic solvents.

The methods provided herein for forming sponges of hyaluronan crosslinked with chitosan can include the steps of:

(a) providing a solution of hyaluronan with a pH of 4.0 to 4.3;

(b) adding a solution of chitosan such that the resultant mixed solution has a pH of 7.2 to 7.5;

(c) adding a water soluble carbodiimide;

(d) stirring the solution formed in (c) for 2 to 4 hours (e.g., 2 hours, 2.5 hours, 3 hours, 3.5 hours, or 4 hours) at a suitable temperature (e.g., room temperature, 15° C., 16° C., 17° C., 18° C., 19° C., 20° C., 21° C., 22° C., 23° C., 24° C., or 25° C.);

(e) washing the hydrogel formed in PBS; and (f) freeze-drying the hydrogel.

HA/chitosan crosslinked materials prepared using the methods described herein can be biocompatible and biodegradable for drug delivery and tissue engineering. They can have excellent biostability against enzymes, because the hyaluronan is covalently crosslinked with chitosanic polymers, which are much more stable biopolymers than HA in vivo. The biostability of HA/chitosan crosslinked materials can be tested using hyaluronidase and lysozyme at 37° C. for 24 to 48 hours. In fact, the crosslinked materials prepared as described in the Examples showed excellent biostability against enzymes.

The degradation rate can be controlled as required by changing the ratio of polymers and EDC used.

As well as the improved biostability of chitosanic polymers compared to hyaluronan, the HA/chitosan crosslinked materials provided herein also can combine other advantages of chitosanic polymers, such as, for example, good bioadhesion properties.

The HA/chitosan crosslinked materials described herein can contain amine groups whose content can be controlled by adjusting the amounts of chitosanic polymers and EDC. Amine groups are important for conjugating bioactive agents such as drugs, proteins and DNA.

HA/chitosan crosslinked materials can be made at a lower cost than other materials composed of hyaluronan crosslinked to itself, as chitosan is cheaper than hyaluronan. Thus, the processes described herein can be simple, cheap, and efficient, providing 100% yield of the desired product.

HA/chitosan crosslinked materials prepared as described herein may be used in a variety of pharmaceutical, medical (including surgical) and cosmetic applications. For example, they may be useful in promoting wound healing, e.g., as dermal wound dressings. Sponges, for example, may be particularly useful as dermal wound dressings or as three-dimensional scaffolds for tissue engineering. The materials provided herein also may be useful in preventing adhesion, e.g., preventing tissue growth between organs following surgery. These materials also may find application in the ophthalmic field, e.g., for vitreous fluid replacement, as corneal shields for delivery of drugs to the eye or as lenticules.

HA/chitosan crosslinked materials also may be useful in surgery as, for example, solid implants for hard tissue augmentation (e.g., repair or replacement of cartilage or bone), or for soft tissue augmentation, as breast implants, or as coating for implants intended for long term use in the body, such as breast implants, catheters, cannulas, bone prostheses, cartilage replacements, mini pumps and other drug delivery devices, artificial organs and blood vessels, meshes for tissue reinforcement, etc. They also may be used as joint lubricants in the treatment of arthritis.

A further use for the materials prepared by the methods described herein is in the delivery of therapeutically active agents including in any of the aforementioned applications. Therapeutically active agents may be, for example, chemotherapeutic agents or biologically active factors (e.g., cytokines), and can include anti-inflammatory agents, antibiotics, analgesics, anaesthetics (e.g., lidocaine), wound healing promoters, cystostatic agents, immunostimulants, immunosuppressants, DNA and antivirals The therapeutically active factors may be bound, either physically or chemically, to the crosslinked HA/chitosan material using, for example, methods known in the art.

Products of the methods provided herein can be characterized using, for example, the following methods.

To measure water absorption capacity, approximately 20 mg of fully dried sample can be immersed in distilled water for 24 hours. The fully hydrated gels can be filtered and residual water on the surface removed using tissue paper. The water absorption capacity (WAC) or swelling degree (SD) can be calculated as follows:

$$WAC=(W-W_0)/W_0 \times 100\%,$$

where $W_0$ is the weight of initial dry sample and W is the weight of fully hydrated gel.

To measure chemical stability, dried samples can be weighed and put in PBS (pH 7.4), 0.1 M and 6 M HCl aqueous solutions or 6 M NaOH aqueous solution respectively. At various intervals, sample dissolution can be observed. If necessary, samples can be filtered and washed with water to neutral pH and then dried and weighed.

Resistance to hyaluronidase digestion can be measured as follows: crosslinked and purified samples (gels, films, sponges, etc.) can be sterilized at 121° C. for 15 minutes, dried by freeze drying, and cut into pieces. A portion (e.g., 20 mg) of each sample can be put in 6 ml PBS (pH:7.4) containing 1000 U hyaluronidase (Sigma Chemical Co., St. Louis, Mo.) and incubated at 37° C. for 24 hours. The solid can be removed and rinsed with PBS. The rinsed and incubated PBS solution can be put together and boiled for 15 minutes to precipitate hyaluronidase and then made up to 25 ml with PBS. The opaque solution can be centrifuged at 4000 RPM for 20 minutes and the clear supernatant can be taken to measure hyaluronan concentration using, for example, a Carbozole assay. Six ml PBS solution containing 1000 U hyaluronidase can be used as a control. The hyaluronan weight loss can be calculated using the following formula:

$$\text{Hyaluronan weight loss} = \{[HA] \times 25/[HA]_0\} \times 100\%,$$

where [HA] (mg/ml) is hyaluronan concentration determined by Carbozole assay and $[HA]_0$ is the original hyaluronan content (mg).

Resistance to lysozme can be measured using a method based on that described by Imoto et al. (*Agric. Biol. Chem.*, 1971, 35:1154) and Kurita et al. (*Carbohydrate Polymers*, 1993, 20:239-245).

Lysozyme (15 mg from egg white, for example, and available from Sigma), can be dissolved in 500 ml of 0.1 M acetate buffer of pH 4.5. A ferricyanide solution can be prepared by dissolving 0.5 g of potassium ferricyanide in 1000 ml of 0.5 M sodium carbonate.

Samples (e.g., 25 mg samples) that have been sterilized (e.g., at 121° C. for 15 minutes), dried (e.g., by freeze drying), and cut into pieces, can be dispersed in 50 ml of 0.1 M acetate buffer at pH 4.5. Twenty-five ml of the lysozyme solution can be added, and the mixture can be incubated at 37° C. for 48 hours. A sample (e.g., 3 ml) of the supernatant can be removed, ferricyanide solution (e.g., 4 ml) can be added, and the mixture can be boiled for 15 minutes. The mixture can be cooled with water for 5 minutes and the absorbance at 420 nm can be measured using UV/Vis. A control reaction can be carried out in the absence of lysozyme. Hydrolysis of the glycosidic linkages of chitosanic polymers can be calculated using calibration with N-acetylglucosamine of known concentration.

Rheological properties of a gel can be analyzed using, for example, a TA Instruments CSL 500 Rheometer (New Castle, Del.) fitted with a 4 cm and 4° cone-plate geometry. The measurements can be carried out at 25° C.

FTIR spectra of cast films, for example, can be obtained using a Perkin-Elmer 1600 Series FTIR instrument. The specimen films can be prepared by casting solutions containing hyaluronan and chitosanic polymers as well as EDC before crosslinking.

The invention will be fuirther described in the following examples, which do not limit the scope of the invention described in the claims.

EXAMPLES

Example 1

This example illustrates the crosslinking of hyaluronan and glycol chitosan in aqueous solution to prepare a hydrogel using EDC.

Solid hyaluronan (0.3 g, MW: $2.06 \times 10^6$, Vitrolife UK Ltd) was dissolved in 30 ml distilled water overnight at room temperature to obtain a homogeneous and clear solution (1%). 1.5 g glycol chitosan (MW: $5 \times 10^5$, degree of deacetylation: 86%, Sigma) was dissolved in 100 ml distilled water overnight. The solution (1.5%, pH: 9.1) was then filtered to remove any insoluble material. The pH value of the hyaluronan solution was adjusted to 4.0-4.3 by adding 0.1 M HCl with stirring. Seventeen ml of the glycol chitosan solution was added to the hyaluronan solution. The mixed solution remained clear and the pH should be between 7.2 to 7.5. After stirring for 30 minutes, 0.26 g 1-ethyl-3-(3-dimethylaminopropyl) carbodiimide methiodide or 0.17 g 1-ethyl-3-(3-dimethylaminopropyl) carbodiimide hydrochloride was dissolved in 2 ml distilled water and then added into the mixed solution under stirring. The clear mixed solution was stirred at room temperature for about 3 hours and a strong hydrogel formed. This hydrogel was then exhaustively washed with PBS (pH:7.4) to remove residual reagents and other small molecules without loss of its properties. The water adsorption capacity was 5400%.

Example 2

This example illustrates formulating a gel into a hydrogel injectable through a 30 Gauge needle.

A hydrogel was prepared using the method described in Example 1. The gel was homogenized for 2 minutes at maximum speed (30 k RPM) using an Omino EZ Connect Homogenizer (Omino International Inc.). The resulting gel was easily injectable through a 30 Gauge needle. The polymer concentration measured by freeze-drying was 1.3%, very close to the theoretical concentration of 1.2% calculated from starting weight of polymer used. Rheological measurements indicated that the elastic modulus G' (6-19 Pa) was higher than the viscous modulus G" (2-11 Pa) and the delta ($\delta$) was 22-30 (FIG. 1), showing the gel to be a very soft and elastic hydrogel.

The hyaluronan weight loss of the sterilized gel was 18% after digestion with hyaluronidase at 37° C. for 24 hours. Only 0.08% of the glycosidic linkage of glycol chitosan was hydrolyzed after digestion with lysozyme at 37° C. for 48 hours.

Example 3

This example illustrates the effects of solution pH on the crosslinking and formation of hydrogel of hyaluronan and glycol chitosan.

Hyaluronan solution and glycol chitosan solution were prepared as described in Example 1. Five hyaluronan solutions (1%) were adjusted to pH 3.5, 4.1, 5.2, 6.4 and 7.5 using 0.1 M HCl. Glycol chitosan solution (1.5%) was then added with stirring. The effects of the various pHs are summarized in Table 1.

TABLE 1

Effects of solution pH on the crosslinking reaction

| | No. | | | | |
|---|---|---|---|---|---|
| | 1 | 2 | 3 | 4 | 5 |
| pH of HA solution | 3.5 | 4.1 | 5.2 | 6.4 | 7.5 |
| pH of mixed solution | 6.6 | 7.3 | 7.7 | 8.3 | 8.6 |
| Appearance of mixed solution | cloudy, complex | clear | clear | clear | clear |
| Time of gelation | — | 3 days | one week | no | no |
| Gel property | | strong | weak | | |

Example 4

This example illustrates that gelation time decreases with increasing solution concentration to crosslink hyaluronan and glycol chitosan.

Three 1% hyaluronan solutions were prepared as described in Example 1. Glycol chitosan solutions of 1%, 1.5%, and 2.5% were prepared. Hyaluronan and glycol chitosan solutions were mixed with stirring, and the pH of the mixed solutions was adjusted to 7.2-7.5. EDC was than added. The times required for gelation were overnight, 3 hours, and 2 hours, respectively, with increasing glycol chitosan concentration.

Example 5

This example illustrates the effects of various weight ratios of hyaluronan/glycol chitosan on the crosslinking of hyaluronan and glycol chitosan.

Hyaluronan (1%) and glycol chitosan (1%) solutions were prepared as described in Example 1. The solutions were pH adjusted and then mixed together with different volume ratios of the respective solutions. EDC was added following the 1:1.2 molar ratio of carboxyl group to EDC. The results are summarized in Table 2.

TABLE 2

Effect of the ratio of hyaluronan/glycol chitosan on their crosslinking

| | Volume ratio (1% HA:1% GC) | | | | |
|---|---|---|---|---|---|
| | 10:5 | 10:8 | 10:7 | 10:10 | 5:10 |
| Weight ratio | 2:1 | 1.8:1 | 1.5:1 | 1:1 | 0.5:1 |
| Time of gelation | one week | overnight | overnight | one week | No |
| Gel property | weak | strong | strong | weak | — |

Example 6

This example illustrates the effects of salt on the crosslinking and formation of hyaluronan and glycol chitosan.

NaCl, KCl and CaCl salts were added into mixed solutions of hyaluronan and glycol chitosan. Salt concentrations varied from 5% to 20% of hyaluronan weight used. The presence of salt did not affect crosslinking of hyaluronan and glycol chitosan. The WAC was between 4500 and 5500%, almost the same as for gels obtained under the same reaction without addition of salt.

Example 7

This example illustrates the preparation of crosslinked films of hyaluronan and glycol chitosan by casting well-mixed solution containing EDC.

Solid hyaluronan (0.2 g) was dissolved in 20 ml distilled water overnight at room temperature to produce a homogeneous and clear solution of 1% hyaluronan. The pH value of the solution was adjusted to 4.0-4.3 by adding 0.1 M HCl with stirring. Eleven to twelve ml of 1.5% glycol chitosan solution was mixed to this hyaluronan solution. The mixed solution remained clear. After stirring for 30 minutes, 0.18 g 1-ethyl-3-(3-dimethylaminopropyl) carbodiimide methiodide was dissolved in distilled water and added the mixed solution under stirring. The clear solution was stirred at room temperature for 30 minutes, and then cast on a Petri dish or glass slide. After drying in air, the film was exhaustively washed with distilled water to remove residual reagents and other small molecules. The film was fully transparent and the water adsorption capacity was 440%. The film was stable in 6 M HCl and 6 M NaOH for at least a week. No weight loss was observed after storage for 2 months in PBS (pH:7.4). The hyaluronan weight loss of the sterilized film was 2.4% after digestion with hyaluronidase at 37° C. for 24 hours.

Figure 3:
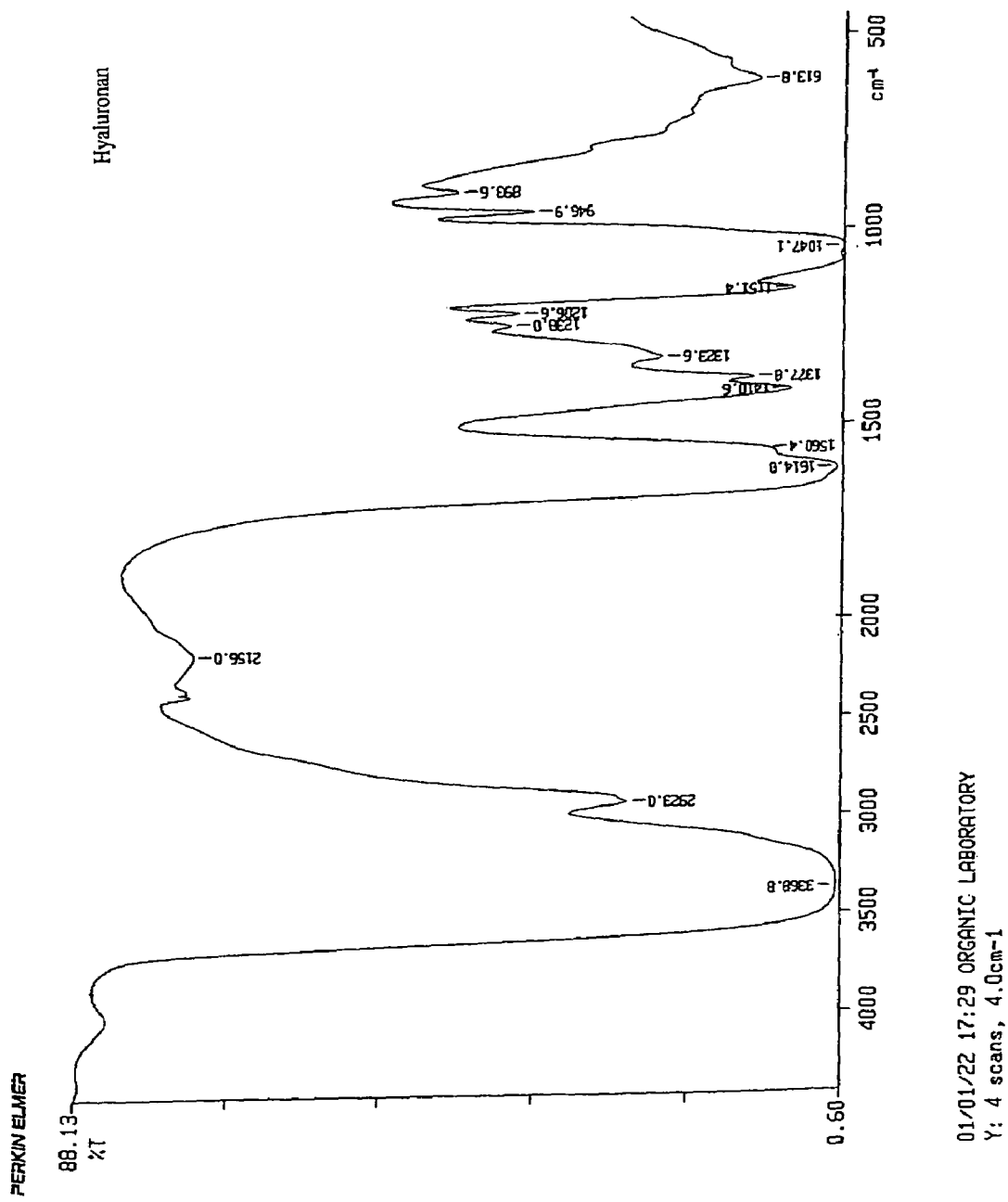
FIG. 3 shows a Fourier Transform Infrared (FTIR) spectra of a cast film of crosslinked HA and glycol chitosan gel.

FTIR spectra of fine films of hyaluronan, glycol chitosan and their crosslinked product showed clearly that the peak at 1591.9 cm$^{-1}$, assigned to the —NH$_2$ group of glycol chitosan, decreased greatly, and a new peak at 1482.5 cm$^{-1}$ appeared (FIG. 3). The new peak was assigned to new amide bond formed between hyaluronan and glycol chitosan.

According to U.S. Pat. No. 5,527,893, FTIR revealed that absorption at 1700 cm$^{-1}$ is found in all the films produced when no amine component has been added. This peak has been assigned to an N-acylurea adduct. In the present work, however, no peak was identified at 1700 cm$^{-1}$ further confirming that the main reaction was amidation between a carboxyl group and an amine group rather than N-acylurea addition of hyaluronan and EDC.

Example 8

This example illustrates the preparation of sponge biomaterials crosslinked hyaluronan and glycol chitosan.

The purified hydrogel prepared in Example 1 was used to fill a cylindrical tube, which was then freeze-dried. The product was a porous cylindrical sponge. The WAC was 710%.

Example 9

This example illustrates the crosslinking of hyaluronan and re-N-acetylated chitosan in aqueous solution using EDC to prepare a hydrogel.

Re-N-acetylated chitosan was prepared following the method described by Maghami et al. (*Macromol. Chemie*, 1988, 189:1953-1956) and Wei Wang (PhD thesis, Nottingham Trent University, UK, 1997, p. 60) using a commercial chitosan (Aber Technologies, MW: 5.05×10$^5$, degree of deacetylation: 98%).

Solid hyaluronan (0.2 g, MW: 2.06×10$^6$, Vitrolife UK Ltd.) was dissolved in 20 ml distilled water overnight at room temperature to obtain a homogeneous and clear solution (1%). The pH was then adjusted to 7.2-7.8. Re-N-acetylated chitosan (1.8 g, MW: 5.7×10$^5$ degree of deacetylation: 48%) was dissolved in 12 ml distilled water overnight. The solution (1.5%, pH: 6.95) was added to the hyaluronan solution with stirring. If there was a precipitate, 0.1 M NaOH solution was added drop wise to get a clear mixed solution. After stirring for 30 minutes, 0.175 g 1-ethyl-3-(3-dimethylaminopropyl) carbodiimide methiodide was added under stirring. The clear mixed solution was stirred at room temperature for about 3 hours, until a hydrogel formed. This hydrogel was exhaustively washed with PBS (pH:7.4) to remove residual reagents and other small molecules without loss of its properties. The WAC was 6000%.

The hyaluronan weight loss of the sterilized gel after digestion with hyaluronidase at 37° C. for 24 hours was 28%. Only 0.44% of the glycosidic linkage of re-N-acetylated chitosan was hydrolyzed after digestion with lysozyme at 37° C. for 48 hours.

Example 10

This example illustrates the preparation of crosslinked films of hyaluronan and re-N-acetylated chitosan (degree of deacetylation: 48%) using well-mixed solutions containing EDC.

Solid hyaluronan (0.2 g) was dissolved in 20 ml distilled water overnight at room temperature to obtain a homogeneous and clear solution (1%). The pH value of the hyaluronan solution was adjusted to 7.2-7.8 if necessary by adding 0.1 M HCl under stirring. Twelve ml of 1.5% re-acetylated chitosan was mixed with the above hyaluronan solution. The mixed solution remained clear (adding a little 0.1 M NaOH solution if mixed solution was cloudy). After stirring for 30 minutes, 0.175 g 1-ethyl-3-(3-dimethylaminopropyl) carbodiimide methiodide was dissolved in distilled water and added to the mixed solution under stirring. The clear solution was kept stirring at room temperature for 30 minutes, then was cast on Petri dish or glass slide. After drying in air, the film was exhaustively washed with distilled water to remove residual reagents and other small molecules. The film was fully transparent and the water adsorption capacity was 1200%. The film was stable in 6 M HCl and 6 M NaOH for at least a week. No weight loss was found after storage for 2 months in PBS (pH: 7.4).

The hyaluronan weight loss of the sterilized gel after digestion with hyaluronidase at 37° C. for 24 hours was 16.7%.

FTIR spectra of fine films of hyaluronan, re-N-acetylated chitosan and their crosslinked product showed clearly that the peak at 1558 cm$^{-1}$ assigned to the —NH$_2$ group of re-N- acetylated chitosan had decreased, and a new peak at 1479.6 cm$^{-1}$ appeared (see FIG. 3). The new peak was assigned to a new amide bond formed between hyaluronan and re-N-acetylated chitosan. In addition, no N-acylurea derivative was detected at 1700 cm$^{-1}$.

Example 11

This example illustrates the crosslinking of hyaluronan and glycol chitosan by casting their well-mixed solutions and then immersing the blend films formed in media containing EDC, in which the blend films cannot dissolve.

Hyaluronan (0.6 g) dissolved in 60 ml distilled water was mixed with 40 ml 1% glycol chitosan aqueous solution. The mixed solution was stirred for 2 hours and a film was cast on a Petri dish. After drying, the film was clear and water-soluble. Five samples of 20 ml 65% IPA+35% water were prepared, each containing 0.12 g EDC. To each sample was added 0.1 g of the above film, and the pH was adjusted pH to 4.75, 7.11, 8.05, 9.04, and 10.10 respectively. After being left overnight, the films were filtered, washed with water, and dried. The crosslinked films were opaque and small broken pieces. The WAC were 400-600%.

Example 12

This example illustrates the crosslinking of hyaluronan and chitosan by casting the well-mixed solutions, and then immersing the blend films in media containing EDC, in which the blend films cannot dissolve.

Hyaluronan (0.6 g) dissolved in 60 ml 0.1 M HCl was mixed with 30 ml 1% chitosan 0.1 M HCl solution. The pH of the mixed solution was 1.91. The mixed solution was stirred for 2 hours and then cast as a film on a Petri dish. After drying, the film was cloudy and soluble in 0.1 M HCl aqueous solution. Five 20 ml mixed solvents of 50% IPA+50% water were prepared, each containing 0.12 g EDC. A tenth of a gram of the above film was added to each sample, and the pH was adjusted to 1.91, 4.75, 7.5 and 9.4 respectively. After being left overnight, the films were filtered, washed with water, and dried. The crosslinked films were opaque. The WAC was 200-300%.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of covalently linking hyaluronan and chitosan, comprising the steps of:
   (a) providing a solution of hyaluronan with a pH of 4.0 to 4.3;
   (b) adding a solution of chitosan such that the resultant mixed solution has a pH of at least 7.2; and
   (c) adding a water soluble carbodiimide.

2. A method as claimed in claim 1, further comprising the step of:
   (d) washing the product of(c) with water or PBS.

3. A method as claimed in claim 1, wherein the pH of the mixed solution is 7.2 to 7.8.

4. A method as claimed in claim 1, further comprising the steps of:
   (d) stirring the solution formed in (c) for 3 hours at room temperature; and
   (e) washing the resultant hydrogel in PBS.

5. A method as claimed in claim 1, further comprising the steps of:
   (d) stirring the solution formed in (c) for 3 hours at room temperature;
   (e) washing the resultant hydro gel in PBS or water; and
   (f) freeze-drying the hydrogel.

6. A method as claimed in claim 1, further comprising the steps of:
   (d) stirring the solution formed in (c) for 30 minutes at room temperature;
   (e) casting the solution into a desired form and allowing it to dry; and
   (f) washing the resultant film with water or PBS.

7. A method as claimed in claim 1, wherein the water soluble carbodiimide is 1-ethyl-3-(3-dimethylaminopropyl) carbodiimide methiodide or 1-ethyl-3-(3-dimethylaminopropyl) carbodiimide hydrochloride (EDC), or a derivative thereof.

8. A method as claimed in claim 1, wherein the pH of the mixed solution is 7.2 to 7.5.

9. A method as claimed in claim 1, wherein mixing the solution at a pH of at least 7.2 in the presence of the water soluble carbodiimide without forming an ionic bond between hyaluronan and chitosan.

* * * * *

UNITED STATES PATENT AND TRADEMARK OFFICE
CERTIFICATE OF CORRECTION

PATENT NO.       : 7,651,702 B2
APPLICATION NO. : 11/132473
DATED            : January 26, 2010
INVENTOR(S)      : Wei Wang Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1287 days.

Signed and Sealed this

Twenty-third Day of November, 2010

David J. Kappos
*Director of the United States Patent and Trademark Office*